(12) United States Patent
Roberts et al.

(10) Patent No.: US 10,983,036 B2
(45) Date of Patent: Apr. 20, 2021

(54) APPARATUS AND METHOD FOR DYNAMIC ACOUSTO-ELASTICITY TECHNIQUE MEASUREMENTS AT SIMULATED SUBSURFACE PRESSURES

(71) Applicant: TRIAD NATIONAL SECURITY, LLC, Los Alamos, NM (US)

(72) Inventors: Peter M. Roberts, Los Alamos, NM (US); Harvey E. Goodman, Houston, TX (US); Marcel C. Remillieux, Los Alamos, NM (US)

(73) Assignees: TRIAD NATIONAL SECURITY, LLC, Los Alamos, NM (US); CHEVRON U.S.A. INC., San Ramon, CA (US)

( * ) Notice: Subject to any disclaimer, the term of this patent is extended or adjusted under 35 U.S.C. 154(b) by 102 days.

(21) Appl. No.: 16/343,986

(22) PCT Filed: Mar. 26, 2017

(86) PCT No.: PCT/US2017/024202
§ 371 (c)(1),
(2) Date: Apr. 22, 2019

(87) PCT Pub. No.: WO2018/080582
PCT Pub. Date: May 3, 2018

(65) Prior Publication Data
US 2019/0339183 A1    Nov. 7, 2019

Related U.S. Application Data

(60) Provisional application No. 62/411,730, filed on Oct. 24, 2016, provisional application No. 62/411,717, filed on Oct. 24, 2016.

(51) Int. Cl.
*G01N 3/36* (2006.01)
*G01N 33/24* (2006.01)
(Continued)

(52) U.S. Cl.
CPC ............. *G01N 3/36* (2013.01); *G01N 15/082* (2013.01); *G01N 29/07* (2013.01); *G01N 29/227* (2013.01);
(Continued)

(58) Field of Classification Search
CPC .. G01N 3/36; G01N 33/24; G01N 2203/0019; G01N 2203/0048;
(Continued)

(56) References Cited

U.S. PATENT DOCUMENTS 2,705,418 A * 4/1955 Francis .............. G01N 15/0826
73/38
8,171,990 B2 * 5/2012 Tchakarov ............ E21B 49/006
166/250.01

(Continued)

OTHER PUBLICATIONS

Jacques Riviere et al: "Frequency, pressure, and strain dependence of nonlinear elasticity in Berea Sandstone", The 3rd EAA European Congress on Acoustics (Forum Acusticum 2002), vol. 43, No. 7, Apr. 16, 2016 (Apr. 16, 2016), pp. 3226-3236, XP055699400, Sevilla, Spain; ISSN: 0094-8276, DOI: 10.1002/2016G L068061 (11 pages).

(Continued)

*Primary Examiner* — Marrit Eyassu
(74) *Attorney, Agent, or Firm* — Esplin & Associates, PC

(57) ABSTRACT

An apparatus (10) and method for performing nonlinear elasticity measurements using the dynamic acousto-elasticity technique (DAET) at simulated subsurface conditions in the laboratory, are described. The current state-of-the-art for measuring nonlinear elasticity parameters using DAET is limited to ambient pressure conditions on the bench-top. The present invention permits nonlinear parameter measurements at controlled sample internal fluid pore pressures (52) and external confining stress (44), (50) conditions.

21 Claims, 8 Drawing Sheets

(51) Int. Cl.
*G01N 29/07* (2006.01)
*G01N 15/08* (2006.01)
*G01N 29/22* (2006.01)

(52) U.S. Cl.
CPC ..... *G01N 33/24* (2013.01); *G01N 2203/0019* (2013.01); *G01N 2203/0048* (2013.01); *G01N 2203/0075* (2013.01); *G01N 2203/0266* (2013.01)

(58) Field of Classification Search
CPC ... G01N 2203/0075; G01N 2203/0266; G01N 33/241; G01N 2291/0232; G01N 2291/02491; G01N 2291/011; G01N 29/07; G01N 29/227; G01N 15/082
USPC .......................................................... 73/825
See application file for complete search history.

(56) References Cited

U.S. PATENT DOCUMENTS

| | | | |
|---|---|---|---|
| 2005/0150273 A1* | 7/2005 | Potter | G01N 3/10 73/38 |
| 2010/0243236 A1 | 9/2010 | Koons | |
| 2011/0050223 A1 | 3/2011 | Balcom | |
| 2011/0154901 A1* | 6/2011 | Calle | G01N 29/348 73/579 |
| 2014/0007667 A1* | 1/2014 | Haggerty | G01N 33/241 73/152.11 |
| 2014/0340082 A1* | 11/2014 | Yang | G01V 3/14 324/309 |
| 2015/0111716 A1* | 4/2015 | Hakimuddin | G01N 33/241 494/10 |

OTHER PUBLICATIONS

Jacques Riviere et al: eA set of measures for the systematic classification of the nonlinear elastic behavior of disparate rocks : Riviere et al. Journal of Geophysical Research: Solid Earth, vol. 128, No. 3, Feb. 25, 2015 (2015-82-25), pp. 1587-1684, XP855699245, ISSN: 2169-9313, DOI: 8.1882/2814JB011718.

Lott Hartin et al: "From local to global measurements of nonclassical nonlinear elastic effects in geomaterials" The Journal of the Acoustical Society of America, American Institute of Physics for the Acoustical Society of America, New York, NY, US, vol. 148, No. 3, Sep. 7, 2016 (Sep. 7, 2016), pp. EL231-EL235, XP812211573, ISSN: 0081-4966, DOI: 18.1121/1.4962373. [retrieved on Sep. 7, 2016].

* cited by examiner

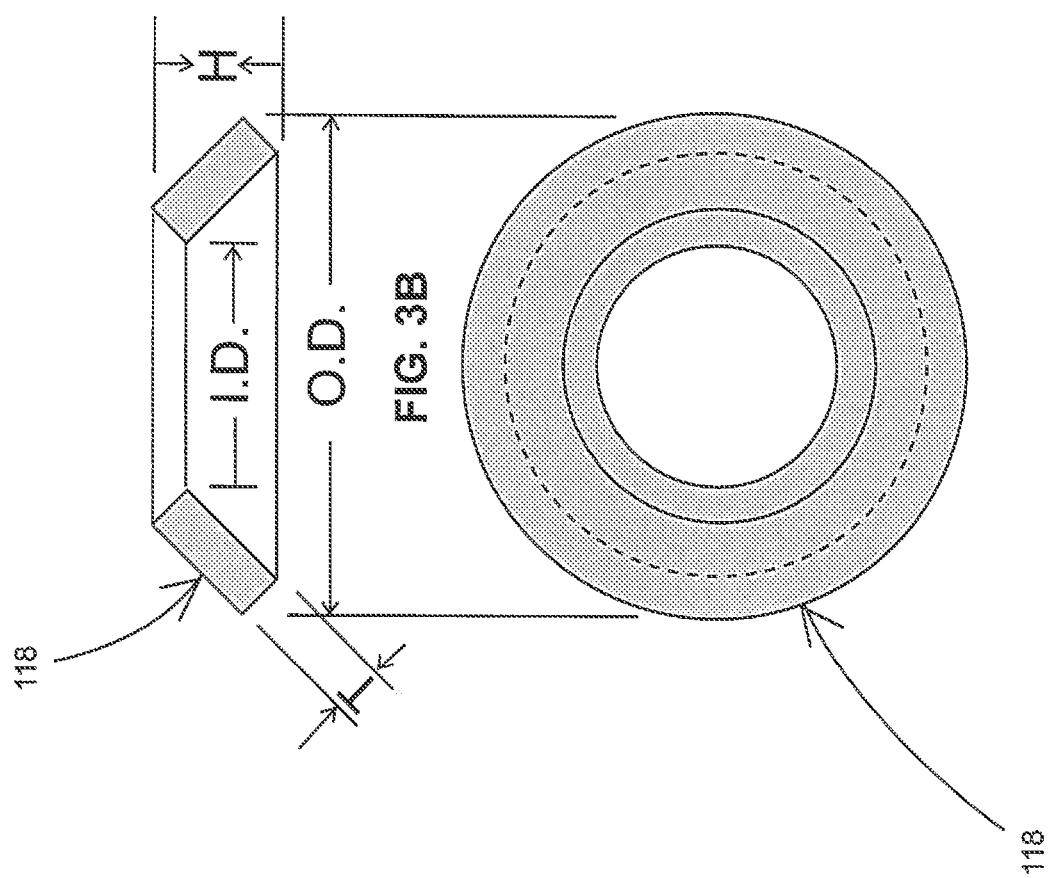

APPARATUS AND METHOD FOR DYNAMIC ACOUSTO-ELASTICITY TECHNIQUE MEASUREMENTS AT SIMULATED SUBSURFACE PRESSURES

CROSS-REFERENCE TO RELATED APPLICATIONS

The present application is a U.S. National Stage Application of International Application No. PCT/US2017/024202, filed on Mar. 26, 2017, which claims the benefit of U.S. Provisional Patent Application No. 62/411,730 for "Pore-Pressure & Stress Controlled Nonlinear Acoustics & Elasticity Measurement Experimental Apparatus Using Dynamic Acousto Elasticity Technique Method At Simulated Subsurface Pressure Conditions" by Peter M. Roberts et al., which was filed on 24 Oct. 2016, and of U.S. Provisional Patent Application No. 62/411,717 for "Time-Reversed Nonlinear Acoustic Downhole Pore Pressure Measurements" by Harvey E. Goodman et al., which was filed on 24 Oct. 2016, the entire contents of which Patent Applications are hereby specifically incorporated by reference herein for all that they disclose and teach.

STATEMENT REGARDING FEDERAL RIGHTS

This invention was made with government support under Contract No. DE-AC52-06NA25396 awarded by the U.S. Department of Energy. The government has certain rights in the invention.

BACKGROUND OF THE INVENTION

Pore pressures are the fluid pressures in the pore spaces in porous formations. Knowledge of pore pressure in a formation is valuable for planning drilling operations and for geochemical and geological analyses. The pore pressure gradient is used in drilling for determining mud weight, which is selected based on pore pressure gradient, wellbore stability and fracture gradient prior to setting and cementing a casing. Drilling fluid is then applied in the form of mud pressure to support the wellbore walls for preventing influx and wellbore collapse during drilling. Geological analyses include initial reserve estimation and fluid contact identification.

Currently, formation pore pressure characterization is limited to direct formation probe contact, either in an open hole or via flow testing from perforations after a wellbore has been cased and cemented. Additionally, pore pressure is measured directly via well production testing with open hole packer isolation. For pore pressure profiling with short turn-around time, the risks of losing the wire line probe assembly, the scarcity of measurements in the open hole, and the costs associated with rig time, result in a great scarcity of accurate pore pressure data.

SUMMARY OF THE INVENTION

To achieve the purposes of embodiments of the present invention, as embodied and broadly described herein, the apparatus for dynamic acousto-elasticity technique measurements at simulated subsurface pressures on a porous elongated cylindrical rock sample having an outer surface, a first face, an opposing second face, an un-stressed length, an axis and a radius, hereof includes: a thin metallic sleeve having an outer surface for enclosing the outer surface of the rock sample and forming a fluid-tight enclosure thereon, the first face and the second face of the rock sample remaining uncovered; a pressure vessel defining a volume for receiving the rock sample, the volume being filled with oil, the pressure vessel having a first flange and an opposing second flange separated by a section having a cylindrical interior; a first pump for providing a pressure to the oil, whereby a chosen radial force is applied to said metallic sleeve; a first pressure distribution plug having a first end in physical contact with the second face of the rock sample, an opposing second end, and a channel through the first distribution plug between the first end and the second end thereof; a first piston in contact with the second end of the first pressure distribution plug, the first piston having a channel therethrough opening into the channel in the first distribution plug; a second pump for moving the first piston against the second end of the first pressure distribution plug, whereby a selected axial force is applied to the second face of the rock sample; a third pump for applying a chosen pressure of fluid to the second face of the rock sample through the channel in the piston and through the channel in the first pressure distribution plug; a second pressure distribution plug having a first end in physical contact with the first face of the rock sample, an opposing second end, an outside surface, and at least one channel between the first end and the outside surface, for permitting fluid to flow through the first face of said rock sample; a disc spring disposed between the second end of the second pressure distribution plug and the first flange, for applying a counterbalancing restoring force to the selected axial force applied by the second pump to the second face of the rock sample; an electromechanical actuator for introducing high amplitude, low frequency (HALF) excitation into the second end of the second pressure distribution plug, whereby axial HALF excitation having a chosen frequency and selected amplitude is introduced into the first face of the rock sample; a first waveform generator for providing electrical excitation to the electromechanical actuator; a pre-load control attached to the first flange for adjusting the pre-load pressure on the actuator from the selected axial force; a linear, variable displacement transducer disposed on the first flange for measuring the displacement of the second end of the second pressure distribution plug; at least one transmitting transducer attached to the outer surface of the thin metallic sleeve for generating low amplitude, high frequency (LAHF) radial excitation pulses in the rock sample; a waveform generator for providing electrical excitation to the at least one transmitting transducer, whereby LAHF excitation pulses are generated by the at least one transmitting transducer; at least one receiving transducer attached to the outer surface of the thin metallic sleeve on the opposite side thereof from the at least one transmitting transducer for receiving the LAHF and generating a voltage therefrom; and a signal processor for receiving the voltage from the at least one receiving transducer.

In another aspect of embodiments of the present invention and in accordance with its purposes the method for measuring dynamic acousto-elasticity properties of a porous elongated cylindrical rock sample having an outer surface, a first face, an opposing second face, an un-stressed length, an axis and a radius, at simulated subsurface pressures, hereof includes: exerting a chosen radial pressure to the outer surface of a thin metallic sleeve having an outer surface for enclosing the outer surface of the rock sample and forming a fluid-tight enclosure thereon, the first face and the second face of the rock sample remaining uncovered; exerting selected axial force on the second face of the rock sample; applying a chosen pressure of fluid to the second face of the rock sample; applying a counterbalancing restoring force to the selected axial force to the first face of the rock sample; introducing high amplitude, low frequency (HALF) excitation into the first face of the rock sample; measuring the displacement of the first face of the rock sample; generating low amplitude, high frequency (LAHF) radial excitation pulses in the rock sample; receiving the LAHF pulses generated in the rock sample and producing a voltage therefrom; and receiving the produced voltage, whereby dynamic acousto-elasticity properties of the rock sample are determined.

Benefits and advantages of embodiments of the present invention include, but are not limited to, providing an apparatus and method for measuring nonlinear parameters at controlled sample internal fluid pore pressures and external confining stress conditions, which will be instrumental in the development of downhole tool dynamic acousto-elasticity technique measurement capability for reliable rock formation fluid pore pressure characterization in cased and open hole environments without direct formation contact.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of the side view of an embodiment of the controlled pore-pressure and confining stress apparatus for nonlinear acoustics and elastic measurements using the dynamic acousto-elasticity technique, while

FIG. 2A is a schematic representation of an expanded side view of the right side of the apparatus shown in FIG. 1A hereof, while

FIG. 3A is a schematic representation of a top view of the disc spring, while FIG. 3B is a schematic representation of a side view thereof.

DETAILED DESCRIPTION OF THE INVENTION

Embodiments of the present invention include an apparatus and method for performing nonlinear (NL) elasticity measurements using the dynamic acousto-elasticity technique (DAET) at simulated subsurface conditions in the laboratory. The current state-of-the-art for measuring NL elasticity parameters using DAET is limited to ambient pressure conditions on the bench-top. The present invention allows NL parameter measurements at controlled sample internal fluid pore pressures and external confining stress conditions, which will be instrumental in the development of the downhole tool DAET measurement capability for reliable rock formation fluid pore pressure characterization in cased and open hole environments without direct formation contact, as described in U.S. Provisional Application No. 62/411,717 identified above. Pore pressure results from fluid present in the pore spaces of a rock sample, while confining stress results from a force applied through a piston or a fluid under pressure exerted on the boundaries or exterior surfaces of the rock volume.

The DAET (Dynamic Acousto-Elasticity) technique for nonlinear elasticity parameter characterization perturbs the selected rock formation measurement region with a High Amplitude Low Frequency (HALF) acoustic wave (compressional, for example) that induces a strain field that is acoustically probed by a Low Amplitude High Frequency (LAHF) acoustic wave. The change in wave speed induced by the HALF strain field oscillation is linked to the nonlinear elastic parameters $\alpha$, $\beta$ and $\delta$ according to Eq. 4 of Provisional Patent Application 62/411,717 as $\Delta c(\varepsilon_p)/c_0 = \frac{1}{2}[\alpha A_p + \beta(\varepsilon_p) + \delta(\varepsilon_p)^2 + A(\varepsilon_p)]$, where $\alpha A_p$ is a DC intercept that depends on the maximum amplitude the pump strain, $A_p$, $\beta$ is the coefficient of $(\varepsilon_p)$, where $\varepsilon_p$ is the instantaneous strain, $\delta$ is the coefficient of $(\varepsilon_p)^2$, and $A(\varepsilon_p)$ represents a function related to the hysteric component of $\Delta c/c_0$.

The modulation of the time-of-flight (TOF) of the probe pulse (LAHF) by the imposed acoustic (HALF or pump) strain is measured. The pump signal period is sufficiently long to allow many pulses to be sent at different times during the pump excitation. Typically, hundreds or thousands of cycles of the HALF pump are used during a DAET measurement (~0.5 to 1 s at the typical kHz frequencies used). The LAHF pulse needs to be sufficiently short (that is, have a center sufficiently high) so individual pulses can be resolved without interfering with one another. Additionally, the LAHF should propagate over a sufficiently short distance (relative to the wavelength of the HALF pump) such that the strain can be considered steady during the pulse propagation.

Figure 1A:
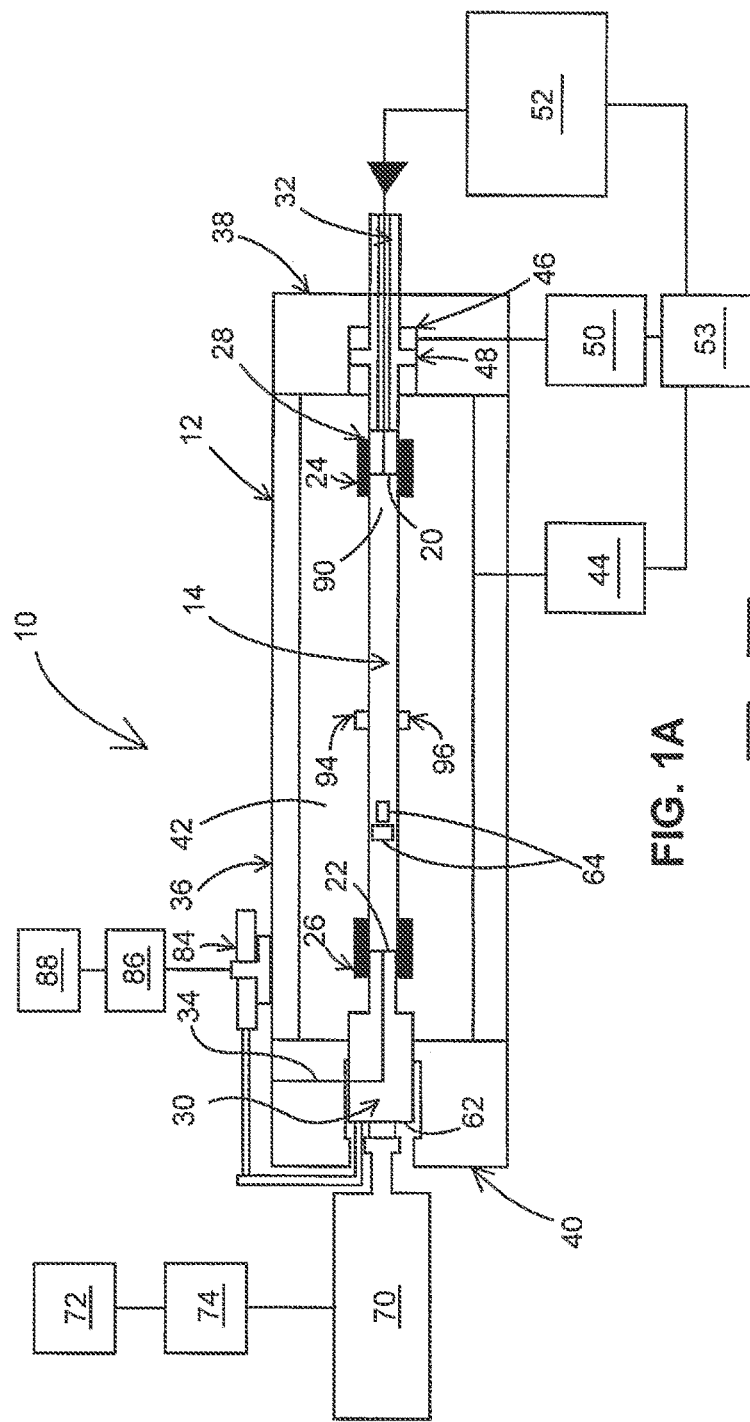
Figure 1B:
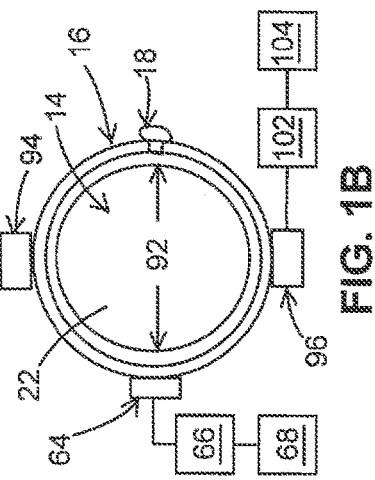
FIG. 1B is an end view of a core sample jacketed with a thin metal foil wrapped around the cylindrical circumference of the core with the seam being sealed with solder.

Reference will now be made in detail to the present embodiments of the invention, examples of which are illustrated in the accompanying drawings. In the FIGURES, similar structure will be identified using identical reference characters. It will be understood that the FIGURES are presented for the purpose of describing particular embodiments of the invention and are not intended to limit the invention thereto. Turning now to FIG. 1A, a schematic representation of an embodiment of the pore-pressure and confining-stress controlled apparatus, 10, for non-linear acoustics and elastic measurements using the Dynamic Acousto-Elasticity Technique. Flow-through triaxial pressure vessel, 12, of the present invention is shown. Pressure vessel 12 is designed to hold cylindrical porous core samples (rock samples), 14, which are 2.54 cm (1 in.) in diameter, and up to 60 cm (24 in.) in length, although other diameters and lengths may be accommodated with modifications of pressure vessel 12. As seen in FIG. 1B, core samples 14 are first jacketed with a thin metal foil, 16, wrapped around the cylindrical circumference of core 14 with the seam being sealed with solder, 18. Although copper foil has been successfully used for this purpose, other metals may also be used. Circular core faces, 20 (second face or right-side face), and, 22 (first face or left-side face), are left open to permit pore fluids to enter and exit the sample. Returning now to FIG. 1A, rubber sleeves, 24, and, 26, are attached to each end of jacketed core 14 for mounting to the inside of the apparatus. Distribution plugs, 28, and, 30, disposed at each end of the sleeves 24 and 26, respectively, accommodate fluid injection into and extraction out of the core by means of tubes, 32, and 34, respectively, drilled through each plug. Pressure vessel 12 includes outer cylinder, 36, and end flanges, 38 (second flange), and, 40 (first flange), for providing support for the components and for providing a sealed volume, 42, which permits pressurized hydraulic oil to surround the circumference of sealed metal Jacketed core 14.

Figure 2A:
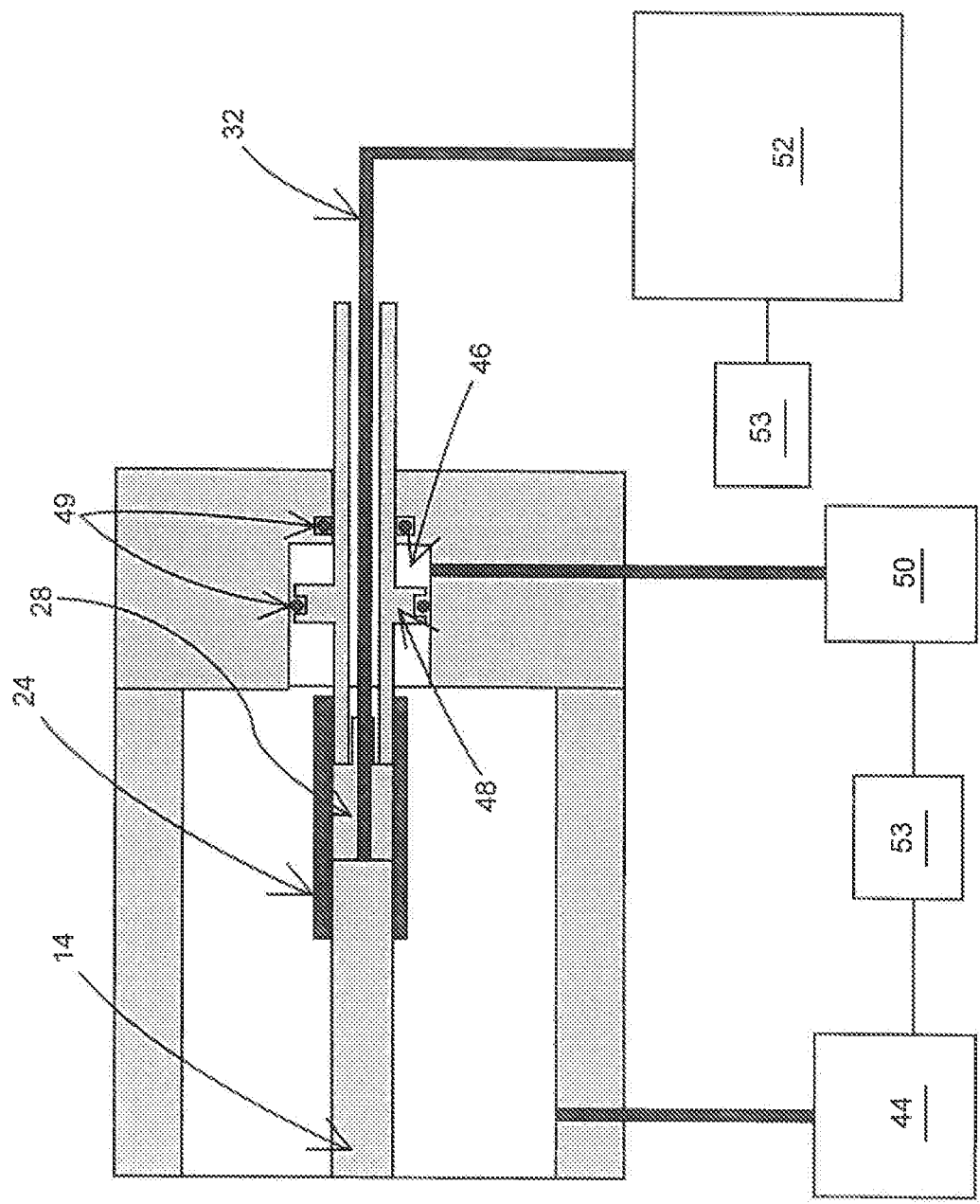

FIG. 2A illustrates static radial confining pressure is applied to volume 42 of pressure chamber 12 using pressure pump, 44. Static axial confinement is applied separately, by means of an oil-filled cylinder, 46, hydraulically attached to load piston, 48, and sealed using O-rings, 49, using pump, 50. Load piston 48 maintains a constant mechanical axial pressure on the distribution plug 28. This static stress is mechanically coupled into and through core sample 14 and into distribution plug 30. Radial and axial pressures can also be connected together to achieve hydrostatic confinement conditions. Constant-pressure oil pumps 44 and 50 are used to apply the static confining stresses to sample 14. The maximum confining pressure (axial and radial) that can be applied to a core sample is 70 MPa (10,000 psi), but more typically, the confining pressure is between 300 psi and 4700 psi. Pore pressure inside the sample is delivered by third constant-pressure fluid pump, 52, by means of tubing 32 attached to an inlet port on distribution plug 28. Pumps 44, 50, and 52, are controlled by computer, 53.

Figure 2B:
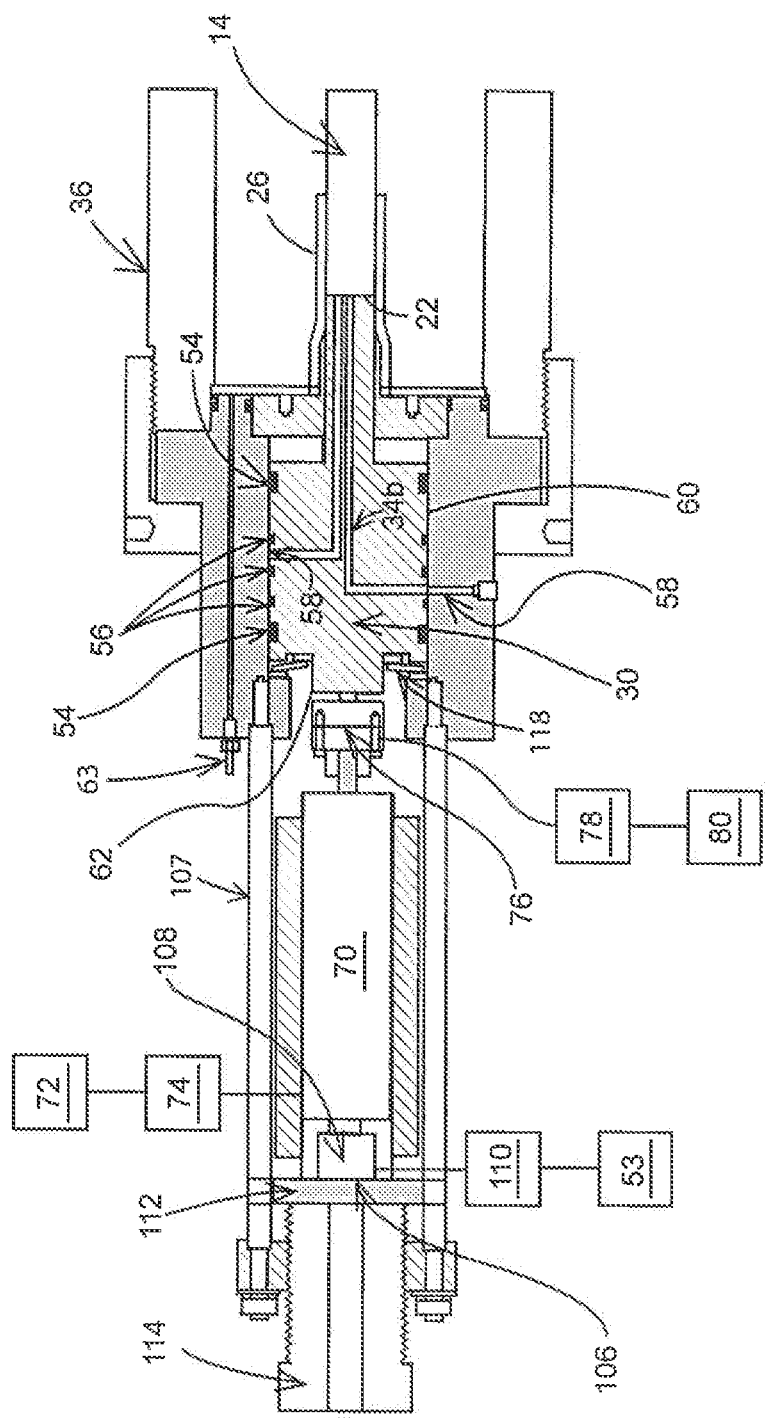
FIG. 2B is a schematic representation of an expanded side view of the left side of the apparatus shown in FIG. 1A hereof.

Turning now to FIG. 2B, distribution plug 30 is allowed to move (or "float") freely in the axial direction by means of slip rings, 54, and O-rings, 56, mounted around its outer circumference. Note that the "fluid lines", 34a, and, 34b, in FIG. 2B comprise holes drilled through floating distribution plug 30. These lines connect to annular channels, 58, machined into the outer circumference of floating distribution plug 30, and located in between O-ring seals 56. This allows pore fluids to enter or exit the sample and apparatus freely, regardless of the circumferential orientation and lateral displacement of floating distribution plug 30. The ability of the plug to move laterally allows external dynamic forces and displacements to be applied directly to the core sample by pushing on its outer end, 62. As stated above, pore pressure inside core 14 is delivered by a third constant-pressure fluid pump 52 to distribution plug 28. An example of the fluid used for pore pressure is 5 weight % KCl dissolved in deionized water, although other solutions may be used. This is used to stabilize the in-situ clay particles present in many natural porous formation core samples of interest. As with the oil-based static mechanical confinement system, pore pressures up to 70 MPa (10,000 psi) can be achieved.

During operation of apparatus 10, core sample 14 is first saturated with the pore fluid by pulling vacuum through the distribution plug 28, with floating distribution plug 30 attached to a graduated burette full of the saturating brine (KCl) solution. The burette and floating distribution plug ports 34a and 34b are initially closed during sample evacuation. When sufficient vacuum is achieved, the vacuum system is closed at distribution plug 28 and the burette is opened at floating distribution plug 30. Brine is pulled into the sample core by the vacuum and fills the connected pore space. The connected pore volume of the sample is measured from the burette's change in fluid volume and is accurate to about +1 mL. Fluid ports 34a and 341 are closed for the duration of the operation of apparatus 10. Desired pore pressure is delivered to the sample from fluid pump 52 through distribution plug 28, as described above. At this stage sample 14 is ready to be interrogated for nonlinear elastic properties using the Dynamic Acousto-Elasticity (DAET) technique.

DAE measurements require numerous electromechanical excitations and measurements for interrogating sample 14. These involve different types of source and receiver devices connected by wires to electronic equipment. Devices that are attached to the sample connect to wires that exit the pressure vessel through high-pressure electrical feed-throughs, 63, located in housing flange 40 that surrounds floating distribution plug 30. Strain gauges, 64, glued to or otherwise in physical contact with copper jacket 16 around the sample (FIG. 1B) are used to monitor the static axial and radial strains that result from the combination of applied mechanical confinement and fluid pore pressure. Strain gauges are pads with conductive elements embedded in them whose resistance changes as they are stretched or compressed. They are attached by wires to amplifier/conditioner, 66, that converts the resistance change into a voltage that is proportional to the strain of the core sample, and measured using signal processor, 68. For each desired combination of applied static pressures (radial, axial and pore), the sample is excited mechanically by dynamic (time-varying) stress applied to the floating distribution plug 30 in the axial direction by electro-mechanical actuator, 70. Typical excitation signals are multiple sinusoidal cycles with frequencies in the 1 Hz to 1000 Hz range. This is the so-called high-amplitude-low-frequency (HALF) "pump" excitation strain. Electro-mechanical actuator 70 may comprise a commercial magnetostrictive actuator electrically driven by a function generator, 72, and amplifier, 74. Actuator 70 is capable of generating dynamic force as high as +900 N (200 lbf) peak-to-peak (P-P) with a maximum displacement of ±70 µm (0.003 in.) P-P. Depending on the rock being studied, axial dynamic strains as high as $10^{-4}$ can be applied with this system.

Measurements of applied axial dynamic mechanical stress variations may be obtained using an electro-mechanical off-the-shelf load cell, 76, placed between actuator 70 and floating distribution plug 30. Load cell 76 produces a voltage proportional to the force applied by the actuator, and is measured using voltage measurement device, 78, and processed by signal processor, 80. Dynamic axial displacement of core face, 22, is measured using a Linear Variable Displacement Transducer (LVDT), 84, which measures the displacement of end 62 of distribution plug 30. LVDT 84 produces a voltage measured by voltage measuring device, 86, and processed using signal processor, 88, which is proportional to the position (displacement) of a magnetic rod inserted into an electromagnetic coil held within the LVDT housing. The rod is mechanically attached to face 62 of floating distribution plug 30, which is in direct mechanical contact with the left-side core face 22. Because right face, 20, of core sample 14 is held at constant axial confining stress, the axial motion of distribution plug 30, as measured by LVDT 84, is a direct measurement of the dynamic change in length of core sample 14 caused by the HALF excitation. The dynamic axial strain of the bulk (core or rock) sample is obtained by dividing the measured axial displacement by the original un-stressed length of the core sample 14. The HALF excitation is performed at sufficiently low frequencies (typically between 10 Hz and 1000 Hz) that wave propagation through core sample 14 does not occur. Core sample 14 behaves as a simple spring where the entire sample compresses and expands dynamically as a bulk unit. Therefore, nonlinear effects that result from the HALF excitation can be measured at any location along the length of core sample 14. Because core sample 14 is always under static compression during operation of apparatus 10 due to the application of static confining stress, the dynamic compression and "expansion" caused by the HALF excitation are relative to the background compression. In other words, "expansion" simply means "less compression".

To probe for nonlinear effects, time-of-flight measurements across diameter, 92, of the sample are made using piezoelectric transducers, 94, and 96, attached to opposite sides of the core's circumference (FIGS. 1A and 1B). Low-amplitude-high-frequency (LAHF) "probe" signals are generated by pulse generator, 98, and amplifier, 100, attached to source piezoelectric transducer 94. The transmitted high-frequency acoustic pulse excites receiver transducer 96, which converts the excitation to a voltage signal that is amplified by amplifier, 102, and electronically processed and recorded by signal processor, 104. LAHF measurements are made numerous times during each cycle of the HALF excitation. Typical frequencies are 100s of kHz (between 200 kHz and 1.5 MHz), which makes the LAHF pulse a propagating acoustic wave. The resulting time-of-flight variations are correlated with the dynamic strain history of the sample which yields the DAET characterization of nonlinear behavior over a wide range of applied static confining and pore pressure settings.

Figure 4:
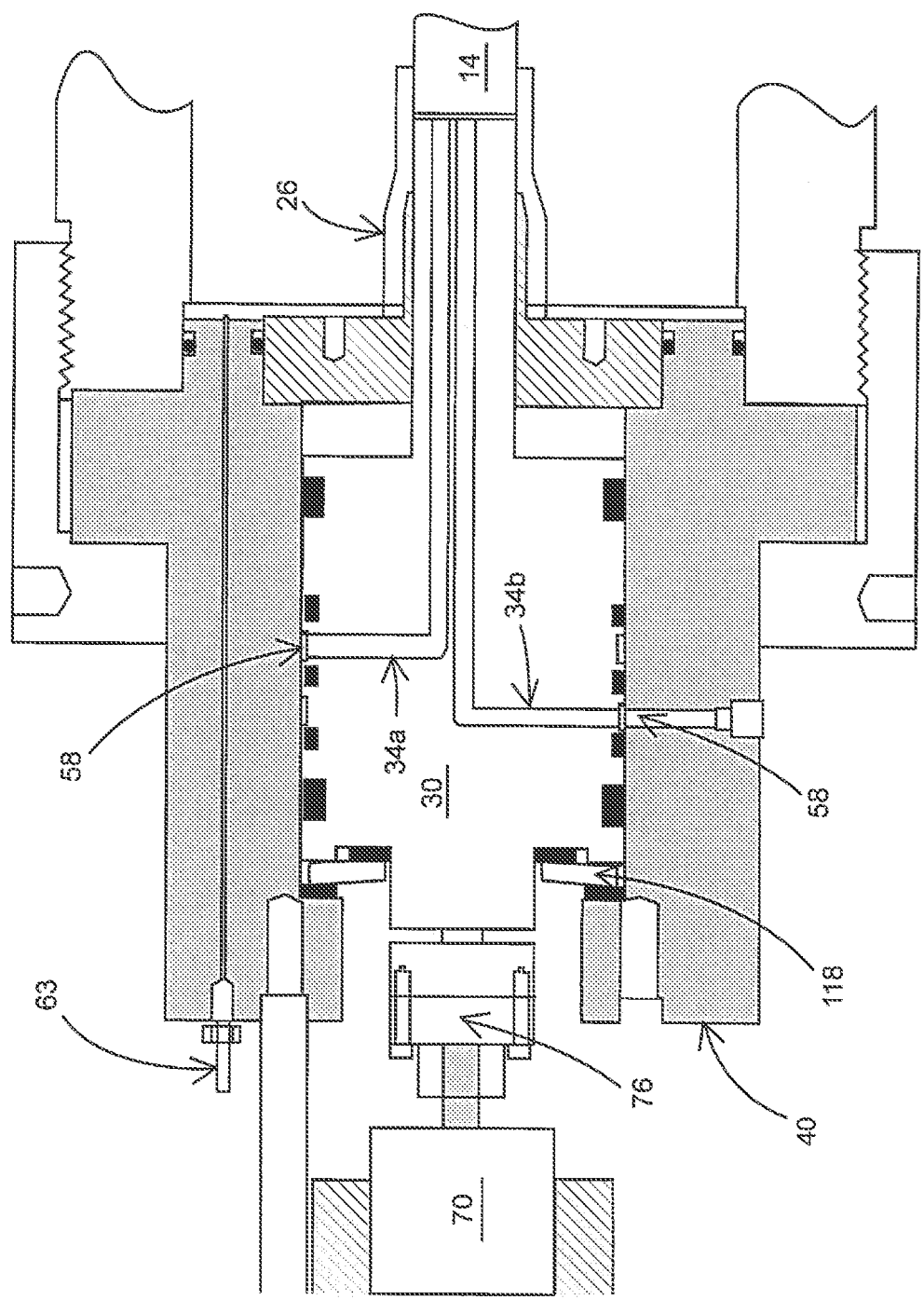
FIG. 4 is a schematic representation of an expanded side view of the location of the disc spring and the floating distribution plug in the first flange.

To allow core sample 14 to respond to relatively low dynamic axial strains generated by actuator 70 without having to first overcome the much higher static loads applied by the radial and axial confining stresses from pumps 44 and 50, floating distribution plug 30 is seated against disc spring, 118, that is, disposed between floating distribution plug 30 and first flange 40, as illustrated in FIGS. 2A, 3A, 3B, and 4. Spring 118 is a commercially available spring shown in detail in FIGS. 3A and 3B. Various heights (H) and thicknesses (T) are available, depending on the desired stiffness (spring constant). A schematic representation of an expanded side view of disc spring 118 and distribution plug 30 is shown in FIG. 4. When a static axial force is applied from piston 48, it is mechanically transmitted through distribution plug 28, core sample 14, floating distribution plug 30 and into disc spring 118. In response, disc spring 118 compresses and applies a counterbalancing restoring force equal and opposite to the applied axial force. Thus, if 1000 pounds of static axial force were applied to the system from piston 48, the disc spring would push back with 1000 pounds of force onto distribution plug 30 to counteract that force. An additional 10 pounds of force, for example could then be applied to core sample 14 by pushing against floating distribution plug 30 with only 10 pounds of force. Without disc spring 118 it would require 1010 pounds of force to achieve the same result. Disc spring 118 therefore permits HALF excitations to be generated by the relatively weak low-frequency electro-mechanical source 70 over a wide range of much higher confining pressures.

Returning to FIG. 2B, a pre-load control system, 106, attached to first flange 40 by rods, 107, for adjusting the pre-load pressure on actuator 70 to ensure that the dynamic HALF pump amplitude remains approximately constant over the entire range of applied static confining pressures, is shown. Without this pre-load control, the output amplitude of actuator 70 would decrease and eventually "stall" as the axial static confining stress increases and the disc spring 118 compresses. This "stalling" of the actuator 70 is caused by the combined system comprised of load piston 48, distribution plug 30, core sample 14 and floating distribution plug 30 moving to the left as the axial confining pressure is increased. The non-constant HALF amplitude in turn would cause the measured nonlinear response to be unreliable. Pre-load control system 106 thus automatically compensates for the applied static confining pressures by maintaining a constant mechanical pressure applied to the left side of the actuator 70. Pre-load system 106 includes a commercially available hydraulic piston, 108, driven by constant-pressure oil pump, 110, similar to those delivering the axial and radial confining pressures to the sample. Piston 108 is attached to mounting plate, 112, and both are inserted between actuator retaining nut, 114, and actuator 70. Constant-pressure pump 110 is set to a desired pre-load by computer 53, which is maintained for all static confining and pore pressures during the measurements, and is monitored using load piston 76.

Having generally described embodiments of the present invention, the following EXAMPLE provides additional details.

EXAMPLE

Figure 5A:
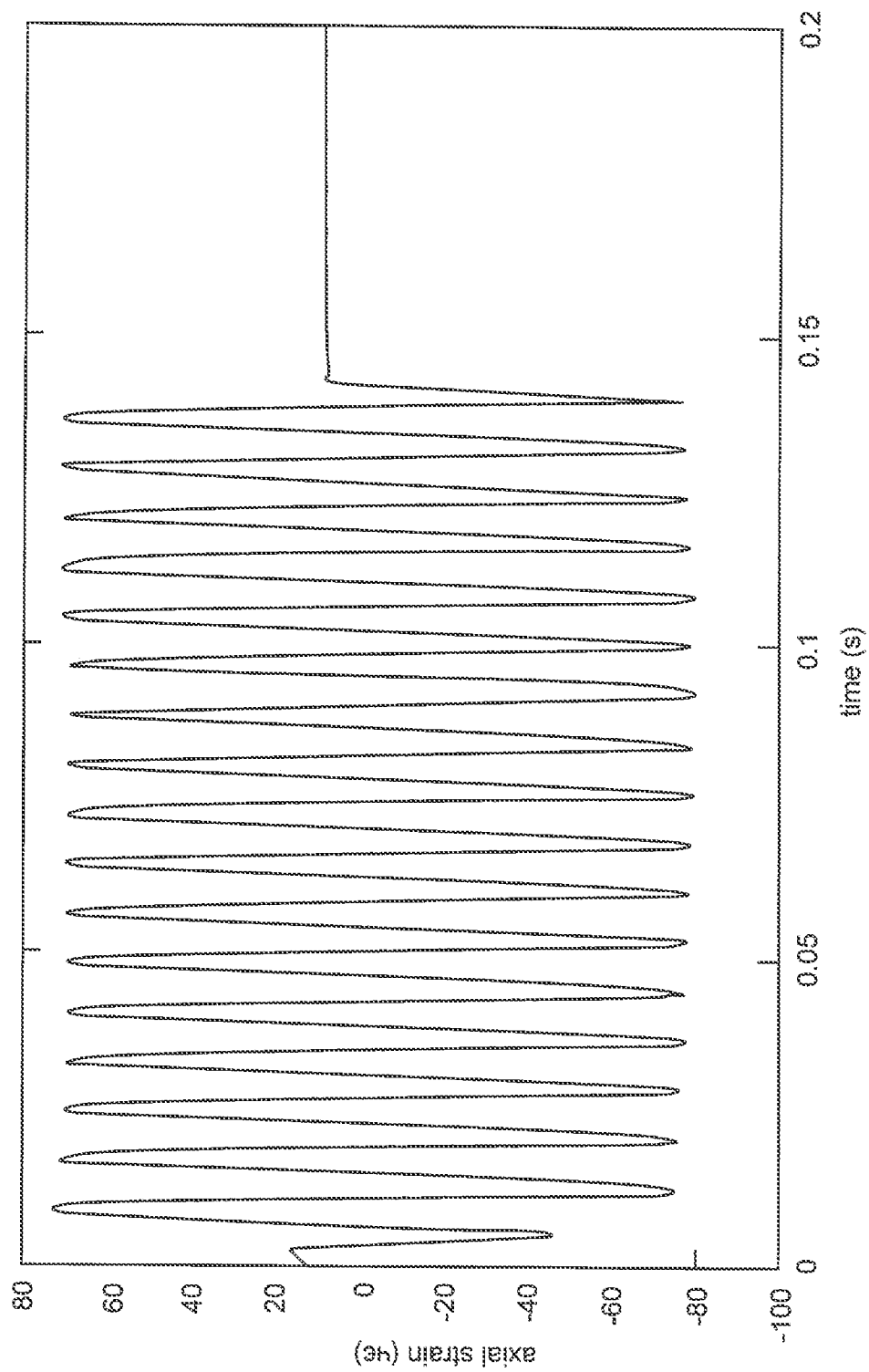
FIG. 5A shows a typical high amplitude, low frequency waveform of the axial strain induced in the core sample by the electro-mechanical actuator.

FIG. 5A shows a typical HALF waveform of the axial strain induced in core sample 14 by electro-mechanical actuator, 70. The HALF signal used was 17 cycles of a 125-Hz sine wave applied for approximately 0.15 s. The vertical axis is axial strain in microstrain units as measured by LVDT 84 and the horizontal axis is time in seconds. As described above, positive strain (compression) and negative strain (expansion) are relative to the background static axial strain induced by the confining pressure. This static background strain has been subtracted from the dynamic HALF strain signal in FIG. 5A. This measurement was obtained for an applied hydrostatic confining pressure (where both radial and axial pressures are identical) equal to 2600 psi and an applied pore pressure equal to 300 psi. The pre-load compensation pressure was 200 psi.

Figure 5B:
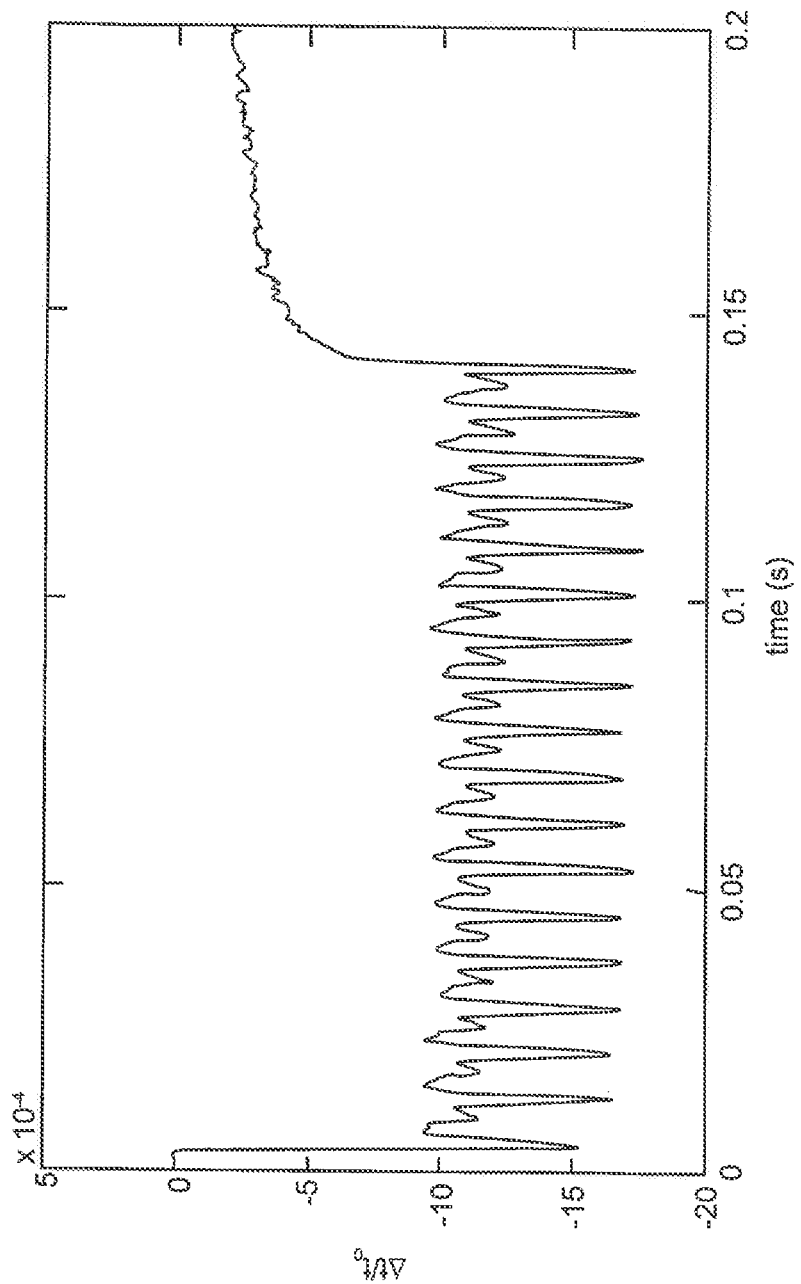
FIG. 5B illustrates repeated measurements of time-of-flight changes for low amplitude, high frequency pulses generated by the transmitting transducer in the core sample and received by the receiving transducer.

FIG. 5B illustrates repeated measurements of time-of-flight changes for LAHF pulses generated by transducer 94 in core sample 14, and received by transducer 96. Measurements are made before, during, and after HALF excitation. Because transducers 94 and 96 are well synchronized, the travel time of these pulses between the transducers can be precisely determined. The travel times for a series of high-frequency pulses (1 MHz was employed) is first measured with core sample 14 being undisturbed dynamically, that is, in hydrostatic equilibrium under both pore and confining pressures that are applied, before the HALF pump is activated. This undisturbed time-of-light is the reference time, $t_0$. Actuator 70 is then activated and measurements of the time-of-flight of the LAHF pulses are continued. During HALF pump excitation, the strain field in the sample oscillates dynamically between $-\varepsilon$ and $+\varepsilon$ relative to the static background confining strain. This dynamic strain induces elastic modulus changes in the core sample due to nonlinear effects. The modulus changes, in turn, are manifested as changes in the time, t, it takes for a LAHF pulse to travel from transmitter 94 to the receiver 96. These time-of-flight changes are denoted as $\Delta t$. FIG. 5B shows that the time-of-flight change relative to the undisturbed reference time, $\Delta t/t_0$, decreases rapidly to an average (steady state) value of approximately $12 \times 10^{-4}$ to $13 \times 10^{-4}$ and then oscillates around that steady-state value in response to each cycle of the HALF excitation.

Figure 5C:
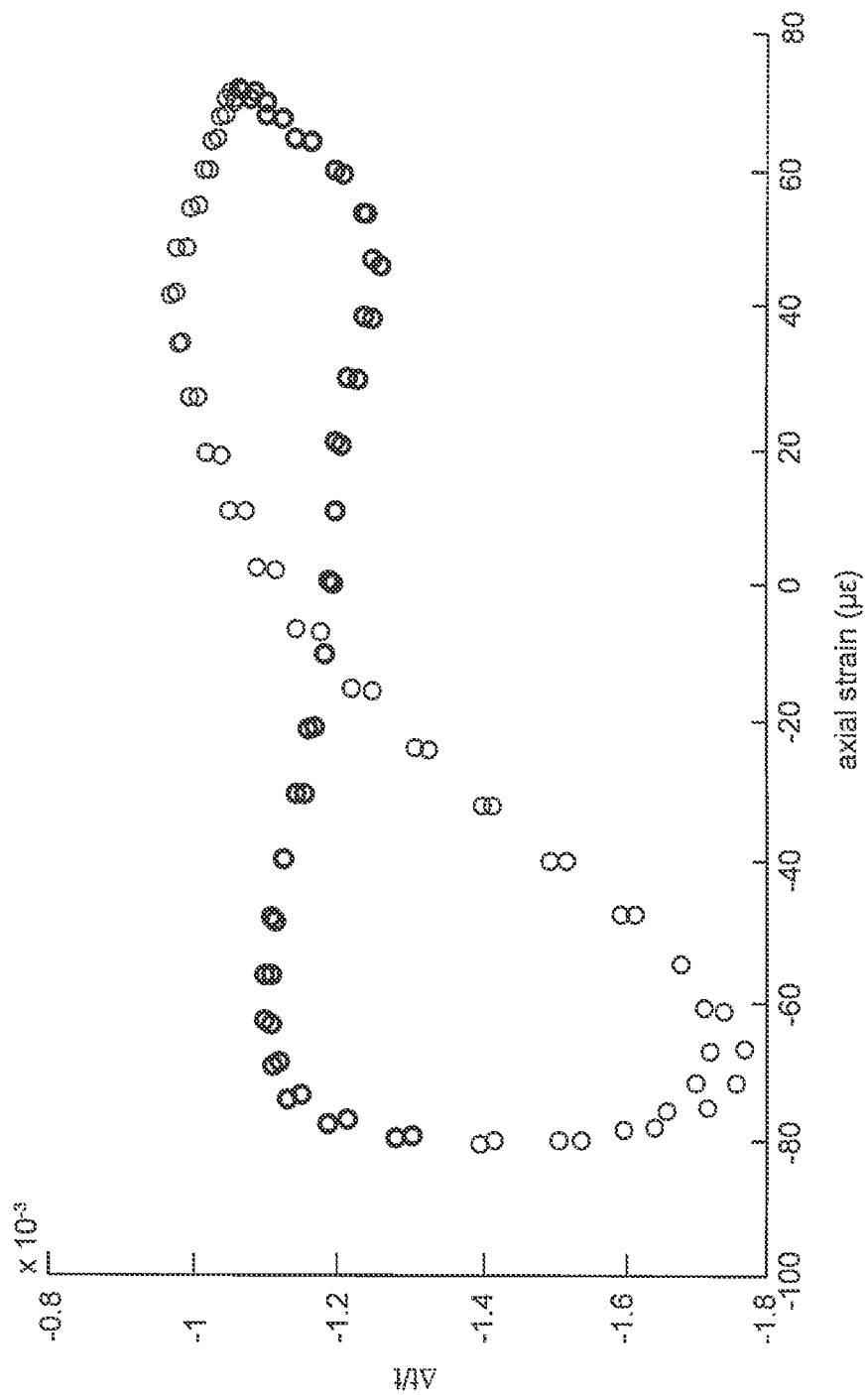
FIG. 5C is a combination of FIGS. 5A and 58, where the relative change of low amplitude, high frequency time-of-flight, $\Delta t/t_0$, is plotted as a function of the high amplitude, low frequency axial strain.

FIG. 5C Is a combination of FIGS. 5A and 5B, where the relative change of LAHF time-of-flight, $\Delta t/t_0$, is plotted as a function of the HALF axial strain. The information contained in FIG. 5C is used to extract the nonlinear parameters of core sample 14, as described above. These measurements may be repeated for many sets of pore pressure and confining pressure settings, in order to extract the nonlinear parameters as a function of these pressure conditions. Note that measurements from only 2 of the 17 HALF cycles in FIG. 5A were used to generate FIG. 5C, and that the pair of results are close in value. This indicates that the measurements are repeatable from one cycle to the next after steady state is reached in FIG. 5B.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the Invention be defined by the claims appended hereto.

What is claimed is:

1. Apparatus for dynamic acousto-elasticity technique measurements at simulated subsurface pressures on a porous, cylindrical rock sample that runs along an axis and has an outer surface formed at a radius from the axis, a first face at one end, and a second face at an end opposite the first face, the rock sample having an un-stressed length from the first face to the second face, the apparatus comprising:
   a metallic sleeve configured to enclose the outer surface of said rock sample and form a fluid-tight enclosure to inhibit fluid exchange through the outer surface of the rock sample, the metallic sleeve being open at opposing ends to leave the first face and the second face of said rock sample uncovered when the metallic sleeve is installed on the rock sample;
   a pressure vessel defining a volume to accommodate the rock sample therein, said pressure vessel having a generally elongate shape with a first flange at one end and a second flange at an end opposite the first flange, pressure vessel further including a hollow section between the first flange and the second flange, the volume formed at least in part by the hollow section containing oil;
   a first pump configured to control radial pressure of the oil within the volume of the pressure vessel to apply a chosen radial force to the metallic sleeve;
   a first pressure distribution plug having a first end, a second end opposite the first end, and a channel through the first distribution plug between the first end and the second end, the first end being configured to physically contact the second face of the rock sample to place the second face of the rock sample in fluid communication with the channel;
   a first piston coupled with the first pressure distribution plug, the first piston having a channel therethrough that is in fluid communication with the channel of the first distribution plug when the first piston is coupled with the first distribution plug;
   a second pump configured to controllably apply a force to the first piston that causes an axial force to be applied to the second end of said first pressure distribution plug by virtue of the coupling between the first piston and the second end of the first distribution plug, whereby a selected axial force is applied to the second face of said rock sample by the first end of the first distribution plug;
   a third pump configured to apply a chosen pressure to fluid within the channels of the first distribution plug and the first piston, such fluid being in contact with the second face of said rock sample;
   a second pressure distribution plug having a first end, a second end opposite the first end, and a channel formed through the second pressure distribution plug from the first end to the second end, the first end being configured to be in physical contact with the first face of said rock sample such that fluid present in the channel of the second distribution plug is communicated to the first face of the rock sample;
   a disc spring disposed between the second end of said second pressure distribution plug and said first flange, the disc spring being configured to apply a counterbalancing restoring force to the selected axial force applied by said second pump to the second face of said rock sample;
   an electromechanical actuator configured to introduce high amplitude, low frequency (HALF) excitation into the second end of said second pressure distribution plug, whereby axial HALF excitation having a chosen frequency and selected amplitude is introduced into the first face of said rock sample;
   a first waveform generator for providing electrical excitation to said electromechanical actuator;
   a pre-load control attached to said first flange for adjusting the pre-load pressure on said electromechanical actuator from the selected axial force;
   a linear, variable displacement transducer disposed on said first flange for measuring a displacement of the second end of said second pressure distribution plug;
   at least one transmitting transducer carried by the metallic sleeve, the at least one transmitting transducer being configured to generate low amplitude, high frequency (LAHF) radial excitation pulses in said rock sample;
   a second waveform generator for providing electrical excitation to said at least one transmitting transducer, whereby LAHF excitation pulses are generated by said at least one transmitting transducer;
   at least one receiving transducer carried by the metallic sleeve configured to receive the LAHF radial excitation pulses, the at least one receiving transducer being further configured to generate a voltage from the received LAHF; and
   a signal processor configured to receive the voltage from said at least one receiving transducer.

2. The apparatus of claim 1, further comprising a load cell disposed between said electromechanical actuator and said second pressure distribution plug, for measuring the mechanical stress imposed on said rock sample by said electromechanical actuator.

3. The apparatus of claim 2, wherein said electromechanical actuator comprises a magnetorestrictive actuator.

4. The apparatus of claim 1, wherein the fluid comprises a solution of 5% KCl in water.

5. The apparatus of claim 1, wherein said signal processor computes a time-of-flight of the low amplitude, high frequency excitation pulses in said rock sample.

6. The apparatus of claim 1, wherein said rock sample is held under static compression during dynamic acousto-elasticity technique measurements.

7. The apparatus of claim 1, wherein the second face of said rock sample is held at a constant axial force during dynamic acousto-elasticity technique measurements.

8. The apparatus of claim 7, wherein the displacement of the second end of said second pressure distribution plug measured by said linear, variable displacement transducer is equal to a displacement of the first face of said rock sample in contact therewith and a dynamic axial strain of said rock sample is obtained from the ratio of the displacement of the first face of the rock sample to the un-stressed length of said rock sample.

9. The apparatus of claim 1, wherein the axial force applied to the second face of said rock sample and the radial force applied to the metallic sleeve are equal.

10. A method for measuring dynamic acousto-elasticity properties of a porous, generally cylindrical rock sample that runs along an axis and has an outer surface formed at a radius from the axis, a first face at one end, and a second face at an end opposite the first face, the rock sample having an un-stressed length from the first face to the second face, the method comprising:
  enclosing the outer surface of the rock sample with a metallic sleeve to form a fluid-tight enclosure around the outer surface of the rock sample to inhibit fluid exchange through the outer surface of the rock sample, the first face and the second face of said rock sample remaining uncovered, the rock sample accommodated within a volume of a pressure vessel, said pressure vessel having a generally elongate shape with a first flange at one end and a second flange at an end opposite the first flange, pressure vessel further including a hollow section between the first flange and the second flange, the volume formed at least in part by the hollow section containing oil, wherein:
    a first pressure distribution plug having a first end, a second end opposite the first end, and a channel through the first distribution plug between the first end and the second end thereof physically contacts the second face of the rock sample to place the second face of the rock sample in fluid communication with the channel; and
    a first piston is coupled with the first pressure distribution plug, the first piston having a channel therethrough that is in fluid communication with the channel of the first distribution plug when the first piston is coupled with the first distribution plug;
  exerting a chosen radial pressure to the metallic sleeve by controlling radial pressure of the oil within the volume of the pressure vessel using a first pump;
  exerting a selected axial force on the second face of said rock sample by the first end of the first distribution plug by using a second pump to controllably apply a force to the first piston that causes an axial force to be applied to the second end of said first pressure distribution plug by virtue of the coupling between the first piston and the second end of the first distribution plug;
  applying a chosen pressure of fluid to the second face of said rock sample by using a third pump to apply a pressure to fluid within the channels of the first distribution plug and the first piston, such fluid being in contact with the second face of said rock sample, wherein a second pressure distribution plug having a first end, a second end opposite the first end, and a channel formed through the second pressure distribution plug from the first end to the second end thereof physical contacts the first face of said rock sample such that fluid present in the channel of the second distribution plug is communicated to the first face of the rock sample;
  applying a counterbalancing restoring force to the selected axial force applied by the second pump to the second face of said rock sample by using a disc spring disposed between the second end of said second pressure distribution plug and said first flange;
  introducing axial high amplitude, low frequency (HALF) excitation having a chosen frequency and selected amplitude into the first face of said rock sample by using an electromechanical actuator to introduce HALF excitation into the second end of said second pressure distribution plug, wherein a first waveform generator provides electrical excitation to said electromechanical actuator and a pre-load control is attached to said first flange to adjust the pre-load pressure on said electromechanical actuator from the selected axial force;
  measuring a displacement of the first face of said rock sample by using a linear, variable displacement transducer disposed on said first flange that measures a displacement of the second end of said second pressure distribution plug;
  generating low amplitude, high frequency (LAHF) radial excitation pulses in said rock sample by using at least one transmitting transducer carried by the metallic sleeve, wherein a second waveform generator provides electrical excitation to said at least one transmitting transducer;
  receiving the LAHF radial excitation pulses generated in said rock sample and producing a voltage therefrom using at least one receiving transducer carried by the metallic sleeve; and
  receiving the generated voltage using a signal processor, whereby dynamic acousto-elasticity properties of said rock sample are determined.

11. The method of claim 10, wherein the fluid comprises a solution of 5% KCl in water.

12. The method of claim 10, wherein a time-of-flight of the low amplitude, high frequency excitation pulses in said rock sample is measured.

13. The method of claim 10, wherein said rock sample is held under static compression during dynamic acousto-elasticity technique measurements.

14. The method of claim 10, wherein the second face of said rock sample is held at a constant axial force during dynamic acousto-elasticity technique measurements.

15. The method of claim 14, wherein a dynamic axial strain of said rock sample is obtained from the ratio of the displacement of the first face of the rock sample to the un-stressed length of said rock sample.

16. The method of claim 10, wherein the axial force applied to the second face of said rock sample and the radial force applied to the metallic sleeve are equal.

17. The method of claim 10, wherein the metallic sleeve comprises copper.

18. The method of claim 10, wherein the low amplitude, high frequency excitation pulses comprise sinusoidal signals having frequencies between 200 kHz and 1.5 MHz.

19. The method of claim 10, wherein the high amplitude, low frequency excitation comprises sinusoidal signals having frequencies between 1 Hz to 1000 Hz.

20. The method of claim 10, wherein chosen pressures of fluid up to 70 MPa (10,000 psi) are applied.

21. The method of claim 10, wherein axial and radial pressures up to 70 MPa (10,000 psi) are applied.

\* \* \* \* \*